(12) United States Patent
Behague et al.

(10) Patent No.: US 7,879,000 B2
(45) Date of Patent: Feb. 1, 2011

(54) METHOD, SYSTEM AND MACHINE FOR COLLECTING A BIOLOGICAL FLUID TO WHICH A SELECTED RATIO OF SOLUTION IS ADDED

(75) Inventors: Maurice Behague, Linselles (FR); Francis Goudaliez, Faches-Thunesnil (FR); Thierry Verpoort, Halluin (FR)

(73) Assignee: Macopharma, Mouvaux (FR)

( * ) Notice: Subject to any disclaimer, the term of this patent is extended or adjusted under 35 U.S.C. 154(b) by 774 days.

(21) Appl. No.: 10/750,143

(22) Filed: Dec. 31, 2003

(65) Prior Publication Data

US 2004/0186408 A1    Sep. 23, 2004

(30) Foreign Application Priority Data

Feb. 3, 2003    (FR) .................................. 03 01195

(51) Int. Cl.
| | |
|---|---|
| *A61M 37/00* | (2006.01) |
| *B01D 11/00* | (2006.01) |
| *B01D 61/00* | (2006.01) |
| *C02F 1/44* | (2006.01) |

(52) U.S. Cl. ............... 604/6.07; 604/4.01; 604/6.01; 604/6.15; 210/645; 210/646; 210/647

(58) Field of Classification Search ................ 604/6.07, 604/4.01, 6.01, 6.15; 210/645–647
See application file for complete search history.

(56) References Cited

U.S. PATENT DOCUMENTS

| | | | |
|---|---|---|---|
| 4,258,723 A | 3/1981 | McCue et al. ................ 128/767 |
| 4,267,837 A | 5/1981 | Purdy et al. .................. 128/275 |
| 4,582,598 A | 4/1986 | Bilstad et al. ................ 210/101 |
| 5,910,252 A * | 6/1999 | Truitt et al. .................. 210/645 |
| 6,113,554 A | 9/2000 | Gilcher et al. ............... 600/573 |
| 7,503,901 B2 | 3/2009 | Behague et al. ............. 604/6.07 |
| 2004/0186408 A1 | 9/2004 | Behague et al. ............. 604/4.01 |

FOREIGN PATENT DOCUMENTS

| | | |
|---|---|---|
| EP | 0 583 148 A2 | 9/1993 |
| EP | 583148 A2 * | 2/1994 |
| EP | 1442758 | 8/2004 |
| EP | 1442759 | 8/2004 |
| FR | 2 808 693 | 11/2001 |

* cited by examiner

*Primary Examiner*—Melanie J Hand
(74) *Attorney, Agent, or Firm*—Baker Botts L.L.P.

(57) ABSTRACT

The invention concerns a method of collecting a biological fluid, in particular blood, with an anticoagulant and/or preservation solution added, in which the biological fluid is collected by natural flow and the anticoagulant and/or preservation solution is added by pumping, the method making provision for measuring the flow of fluid collected and slaving the pumping speed to the measured flow, so as to obtain continuously during collection a given ratio between the quantity of fluid collected and the quantity of anticoagulant and/or preservation solution added. The invention also concerns a collection machine and bag system for implementing the method.

12 Claims, 5 Drawing Sheets

METHOD, SYSTEM AND MACHINE FOR COLLECTING A BIOLOGICAL FLUID TO WHICH A SELECTED RATIO OF SOLUTION IS ADDED

PRIORITY CLAIM

The present application claims priority under 35 U.S.C. §119(d) to French Patent Application Ser. No. 03/01195, filed Feb. 3, 2003.

FIELD OF THE INVENTION

The invention concerns a method of collecting a biological fluid to which an anticoagulant and/or preservation solution is added, a machine for implementing this method and a bag system for collecting a biological fluid using such a machine.

BACKGROUND

It is desirable to collect a variety of biological fluids for later use or testing. In particular whole blood or blood components are often collected for later use in patients. Blood or blood components are often collected from the donor in a collection bag. It is recommended that the blood be collected in a sterile fashion and have an anticoagulant and/or preservation solution added at the time of collection so as to allow its subsequent use and the best sanitary safety conditions. Prior to collection, the collection bag is normally filled with the anticoagulant and/or preservation solution.

One of the problems posed by inclusion of an anticoagulant and/or preservation solution in the collection bag is that, in order to produce a homogeneous mixture of the fluid and the solution contained in the bag, it is necessary to agitate the collection bag, which complicates the collection process and does not ensure a proper mixture.

Another problem concerns obtaining a given ratio between the quantity of fluid collected and the quantity of anticoagulant and/or preservation solution added. This problem occurs because, particularly when collecting blood, the quantity of anticoagulant and/or preservation solution present in the collection bag is fixed at a certain value so that the blood can be used in the medical field. When the anticoagulant and/or preservation solution is present in the collection bag prior to collecting the fluid, the ratio of solution to fluid is correct only for a given quantity of fluid collected. Additionally, this ratio of solution to fluid is considerably higher at the start of fluid collection or if collection is interrupted before the entire quantity of fluid required is collected. In the case of blood, this may result in a reduction of the quality of the blood by lysis of the red corpuscles and deterioration of the functionality of the platelets. The blood collected may deteriorate to the point where it becomes unusable.

To solve this problem, it has been proposed, in particular in FR 2,808,693 and U.S. Pat. No. 6,113,554, to place the anticoagulant and/or preservation solution in a bag separate from the collection bag and to supply the collection bag with solution simultaneously during collection of the fluid. These approaches do not sufficiently solve the problem, however.

First, a problem persists concerning obtaining a proper ratio between the quantity of fluid collected and the quantity of anticoagulant and/or preservation solution added. The ratio is obtained either by using a specific bag system or by using a complex pump structure, which complicates use and substantially increases the cost of fluid collection.

Second, another problem persists relating to pumping the fluid which, by imposing a flow on the fluid collected, is necessary for obtaining the desired ratio in previous systems. For safety reasons and when collecting blood from a donor, it is then desirable to use a pressure sensor for the fluid upstream of the pump in order to prevent any risk of collapse of the donor's vein. This sensor, apart from its complexity and cost, may give rise to problems of asepsis if it is based on a gaseous exchange between the inside and outside of the collection system. In addition, the pumping is a source of discomfort and insecurity for the donor.

SUMMARY OF THE INVENTION

The invention aims to resolve these problems by proposing in particular a collection method which is simple to implement, which is comfortable and safe for the donor and which makes it possible to obtain continuously during collection a given ratio between the quantity of fluid collected and the quantity of anticoagulant and/or preservation solution added.

To this end, and according to a first aspect, the invention concerns a method of collecting a biological fluid, in particular blood, with an anticoagulant and/or preservation solution added, in which the biological fluid is collected by natural flow and the anticoagulant and/or preservation fluid is added by pumping. The method includes measuring the flow of fluid collected and slaving the pumping speed to the measured flow rate, so as to obtain continuously during collection a given ratio between the quantity of fluid collected and the quantity of anticoagulant and/or preservation solution added.

According to one embodiment, measurement of the flow of fluid collected is made by calculating the variation in weight of the fluid collected, and the pumping of the anticoagulant and/or preservation solution is carried out by a peristaltic pump whose speed of rotation is variable according to the fluid flow rate measured.

According to a second aspect, the invention concerns a collection machine for implementing the method according to the invention, including a device for measuring the flow of fluid collected and a device for pumping the anticoagulant and/or preservation solution. The pumping device is able to slave the pumping speed to the fluid flow rate determined by the measuring device.

According to one embodiment, the measuring device may measure the weight of fluid collected and calculate its variation over time. The pumping device includes a peristaltic pump with a single head which is able to rotate at variable speeds.

According to a third aspect, the invention concerns a bag system for collecting a biological fluid using a machine according to the invention, the system including, in closed circuit, a fluid collection device, a bag containing an anticoagulant and/or preservation solution for the fluid collected, and a collection bag intended to receive the fluid collected with the anticoagulant and/or preservation solution added. The collection bag is in fluid communication with the collection device by way of a first flexible tube and with the bag containing the anticoagulant and/or preservation solution by way of a second flexible tube.

According to one embodiment, the bag system may have no means for measuring the pressure within the system.

Other objects and advantages of the invention will be apparent from the description which follows taken with reference to the accompanying drawings.

DETAILED DESCRIPTION

The following description provides details of selected embodiments of the invention.

Figure 1:
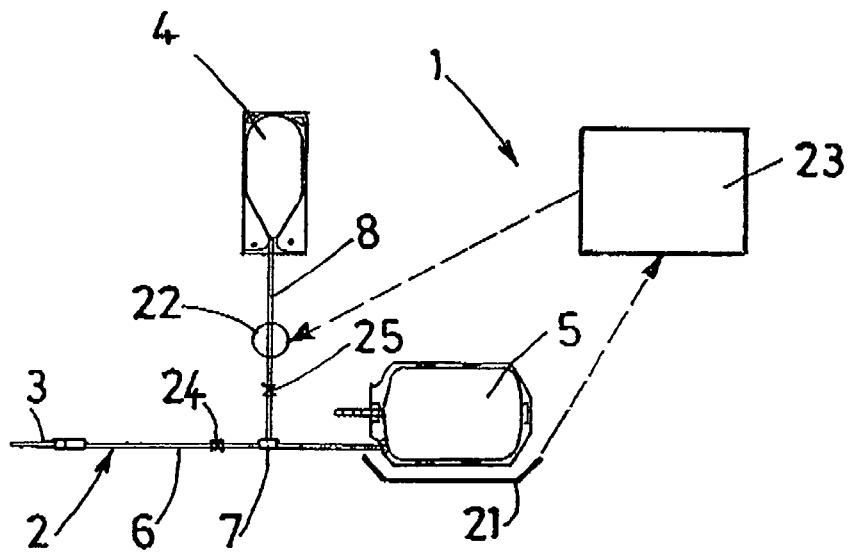
FIG. 1 depicts schematically the functioning of a collection machine according to a first embodiment of the invention, in which a bag system is disposed.

FIG. 1 depicts bag system 2 including collection device 3 for collecting a biological fluid from a patient, at least one bag 4 containing an anticoagulant and/or preservation solution for the fluid collected, and at least one collection bag 5 intended to receive the fluid collected with the anticoagulant and/or preservation solution added.

In one embodiment, bag system 2 is sterilized and packaged in sterile packaging.

Collection device 3 may include in particular needle 42 allowing access to the vein of the donor and cap 43 protecting needle 42. In addition, slidable needle protector 44 may be placed on first tube 6.

Collection bag 5 is in fluid communication with collection device 3 by way of first flexible tube 6. Bag 4 containing an anticoagulant and/or preservation solution is in fluid communication with collection bag 5 by way of second flexible tube 8 connected at connector 7 to first tube 6. This connector is a three-way junction to which there are connected a first part of first tube 6 coming from collection device 3 and second tube 8 and a second part of first tube 6 in the direction of collection bag 5.

According to one embodiment, the part of first tube 6 included between connector 7 and collection bag 5 is of sufficient length to obtain a homogeneous mixture between the fluid collected and the anticoagulant and/or preservation solution, before the mixture reaches the inlet orifice of collection bag 5. The length of this part of first tube 6 may be appreciably greater than 15 cm, for example around 25 cm.

Figure 2:
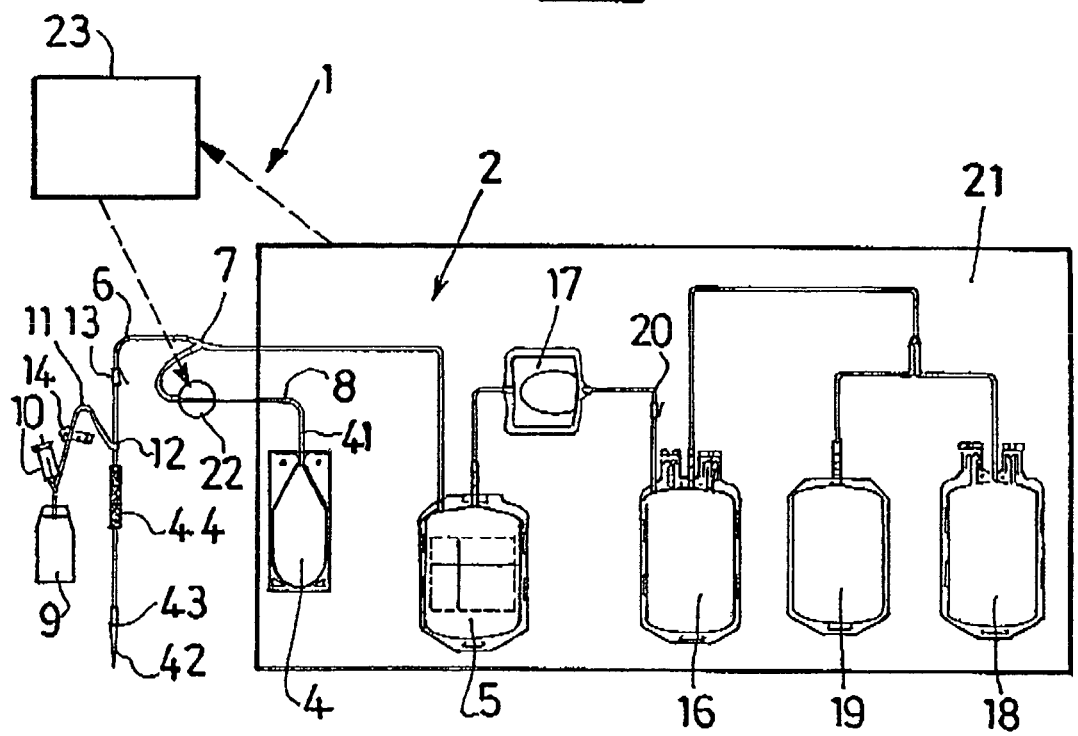
FIG. 2 depicts schematically the functioning of a collection machine according to a second embodiment of the invention, in which a bag system is disposed.

FIG. 2 depicts bag system 2 including, in addition to the bag system depicted in FIG. 1, sampling bag 9 intended to receive the first milliliters of blood collected, and lateral sampling device 10 associated with sampling bag 9 so as to allow the taking of samples by tubes under vacuum.

Sampling bag 9 is in fluid communication with collection bag 5 by way of two flexible tubes 6 and 11 connected at connector 12 in the form of a three-way junction.

Sampling bag 9 and collection bag 5 may be filled by natural flow, that is to say gravity and the venous pressure of the donor. A natural flow based on venous pressure and gravity offers superior comfort and safety to the donor.

Clamps 13 and 14 may be situated respectively on first flexible tube 6, downstream of connector 12, and on flexible tube 11. Clamps 13 and 14 make it possible to direct the first milliliters of fluid collected to sampling bag 9 when clamp 13 is closed while clamp 14 is open. When sampling bag 9 is full, clamp 14 may be closed and clamp 13 may be opened so as to direct the fluid collected to collection bag 5.

Circuit openers may be provided at connector 12 and at the inlet and outlet orifices of the bags containing blood or blood components. Circuit opener 41 is in particular disposed on the second tube, at its end in fluid communication with bag 4 containing the anticoagulant and/or preservation solution in order to prevent the anticoagulant and/or preservation solution from flowing backwards during sterilization of the system, in particular as steam.

Moreover, it is preferable for the circuit opener not to be situated in the passage for flow of the blood between collection device 3 and collection bag 5 in order to lessen any risk of hemolysis of the blood collected at the time of collection.

In order to perform the steps of filtration and separation of the various constituents of the blood, collection bag 5 may be in fluid communication, by way of fourth flexible tube 15, with satellite bag 16. Leukoreduction filter 17 may be situated between collection bag 5 and satellite bag 16.

Satellite bag 16 may be in fluid communication with one or more other satellite bags, for example satellite bag 16 may be in fluid communication with two other satellite bags 18 and 19.

Clamp 20 may be provided on flexible tube 15 between collection bag 5 and leukocyte-removing filter 17.

Figure 4A:
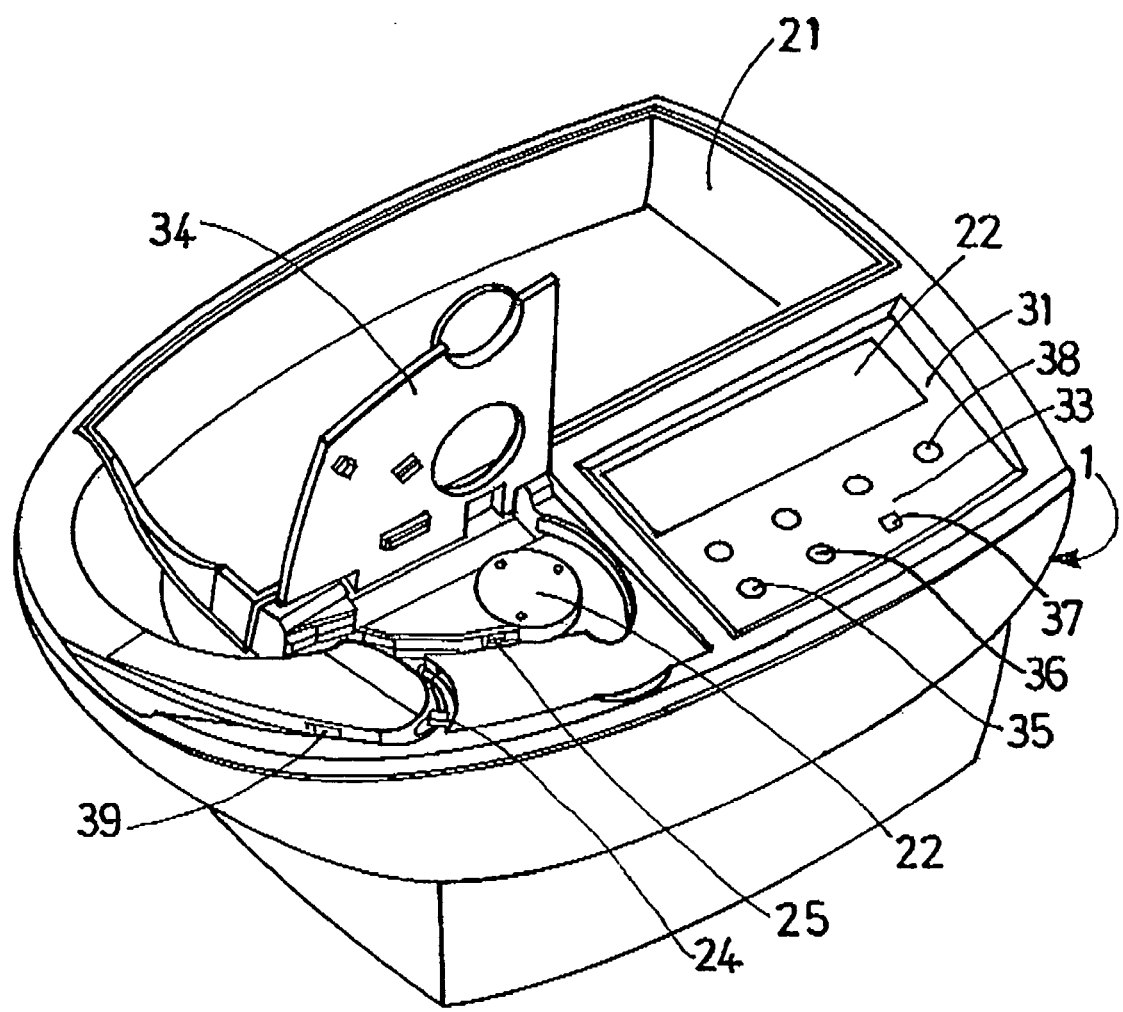
FIG. 4A depicts a front perspective view of the collection machine.
Figure 4B:
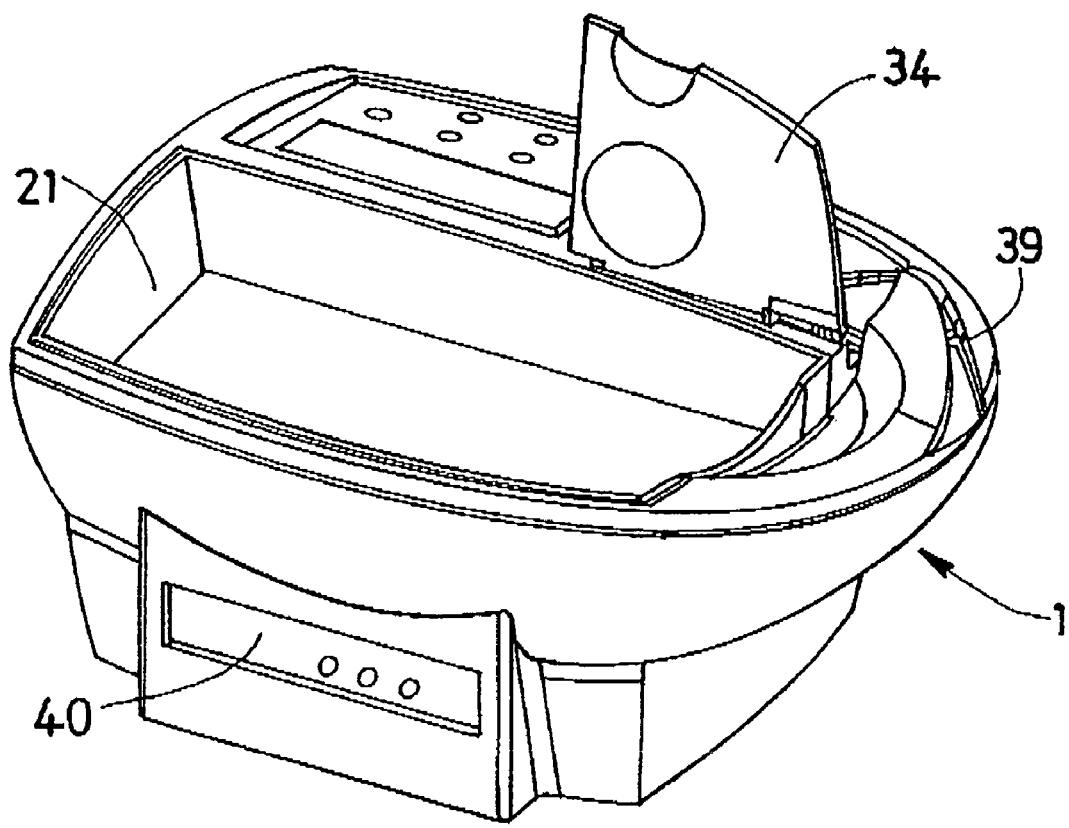
FIG. 4B depicts a rear perspective view of the collection machine.

The bag system described above may be disposed in the placement device of a collection machine as depicted in FIGS. 4A and 4B.

FIG. 4A is a perspective view of the front face of collection machine 1. Collection machine 1 includes weighing device 21, of sufficiently large size to accept bag system 2 as described above.

The collection machine also includes pumping device 22 having a peristaltic pump with a single head which is able to move in rotation at variable speeds in order to pump the anticoagulant and/or preservation solution. Biological fluid may collected by natural flow, that is to say gravity and the venous pressure of the donor. Thus bag system 2 may lack a means for measuring the pressure within the system.

Figure 3:
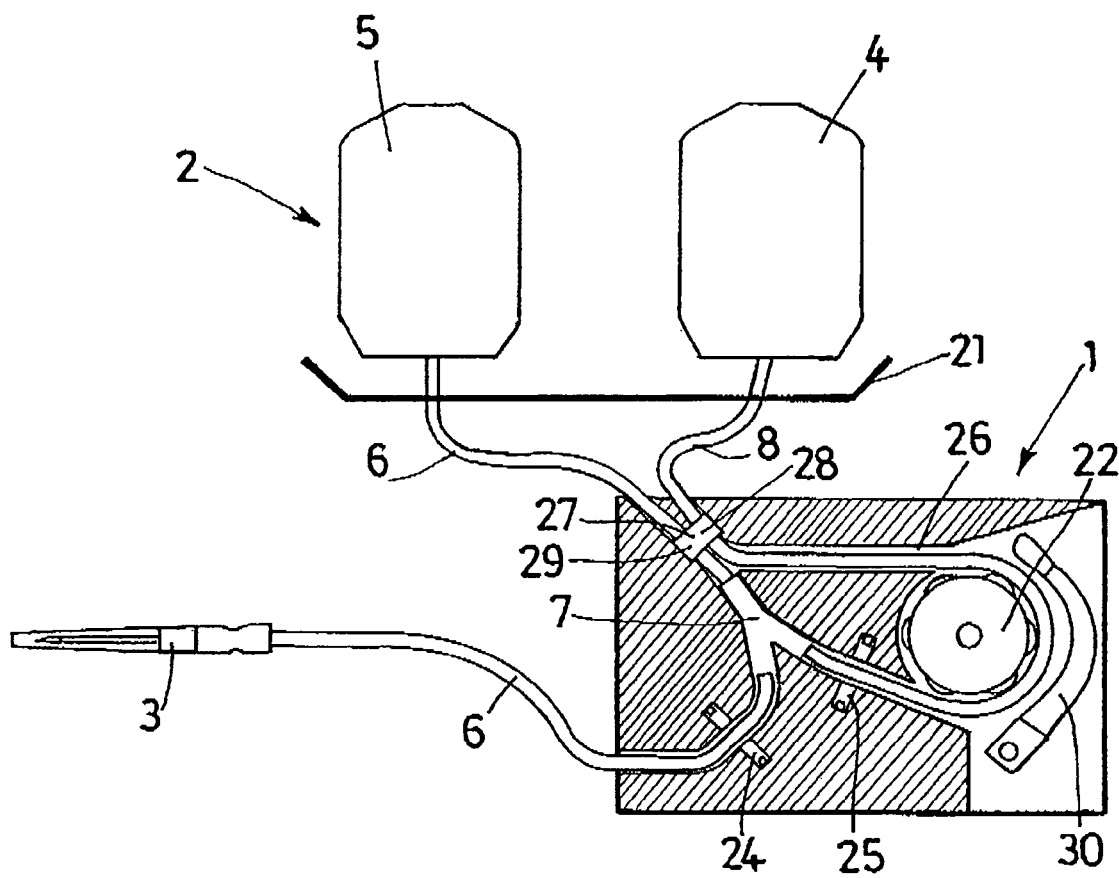
FIG. 3 depicts schematically a bag system disposed on the placement device of a collection machine according to the invention.

As depicted in FIGS. 1 and 2, weighing device 21 makes it possible to know instantaneously the weight and the variations in weight of the fluid collected and thus the flow of fluid collected. For this purpose the whole of bag system 2 as depicted in FIGS. 2 and 3 is placed on weighing device 21. The tare weight is weighed by weighing device 21 after the placement of bag system 2, in order to take account of the weight of bag system 2 before collection of the biological fluid. After a negligible short period (corresponding to the circulation of the solution in tubes 6 and 8), the weight may be measured again and compared to the tare weight. Variations in weight determined by weighing device 21 may then be correlated with the flow of fluid collected. The anticoagulant passes from bag 4 containing the anticoagulant and/or preservation solution to collection bag 5. Because these two bags 4 and 5 are both on weighing device 21 the circulation of the solution does not give rise to any variations in weight.

Peristaltic pump 22 includes a compression head around which there is disposed part of second flexible tube 8. It is possible to slave the flow of the solution to the variations in weight of the fluid collected using control electronics 23 for the motor of pump.

Control electronics 23 translate the variations in weight into flow of fluid collected using a calculation taking into account the density of the fluid collected. Control electronics 23 then determine the appropriate flow of the anticoagulant and/or preservation solution according to a preset ratio and adjust the speed of rotation of peristaltic pump 22 in order to supply the appropriate flow of solution to collection bag 5.

According to an embodiment depicted in FIG. 1, the entire bag system except for bag 4 containing the anticoagulant and/or preservation solution may be placed on weighing device 21. However, it is then necessary to take into account, in addition to the tare weight normally measured, a constant determined by the variation in weight related to the introduction of anticoagulant and/or preservation solution into collection bag 5.

According to a particular embodiment of the invention, optical sensors may be added to machine 1. First optical sensor 24 may be placed on first tube 6 between collection device 3 and connector 7, preferably between connectors 7 and 12. This sensor 24 detects the presence of blood, in order to verify that the blood is circulating suitably within first tube 6. It also checks that there is no air or anticoagulant and/or preservation solution going back towards collection device 3, and therefore towards the donor. This optical sensor may for example be replaced or supplemented by an ultrasonic sensor for detecting flow reversals more finely.

A second optical sensor 25 may be placed on second tube 8 between the head of peristaltic pump 22 and connector 7. This sensor 25 detects the presence of anticoagulant and/or preservation solution in order to check that the anticoagulant and/or preservation solution is circulating suitably within second tube 8.

Machine 1 also includes a placement device designed to receive bag system 2 as depicted in FIG. 3. The placement device includes groove 26 in which the user places tubes 6 and 8 and curved device 30 which may be provided for supporting second tube 8 on peristaltic pump 22 in order to allow correct functioning of the latter. Machine 1 also includes automatic clamp 39 and cap 34 which protects and ensures optimum maintenance of the placement of the bag system in groove 26 of machine 1. Curved device 30 provided for supporting second tube 8 on peristaltic pump 22 moves away from second tube 8 when cap 34 is opened.

When peristaltic pump 22 is in movement, the rollers of pump head 22 successively compress the section of second tube 8 against curved device 30 so as to ensure the movement of the anticoagulant and/or preservation solution in the second tube.

Collection machine 1 also includes interface 31 which is divided into two areas, display 32 and keyboard 33, as depicted in FIG. 4A. Display 32 gives the user of the machine various information: it displays general information such as the date, time or the battery level; information concerning the current collected donation, the number of the donation collected, the volume collected, the duration of the collection or the volume of blood required; as well as error messages when the flow of fluid collected is not correct or when cap 34 of machine 1 is not closed.

Keyboard 33 includes a certain number of keys having various functions. Standby key 35 switches collection machine 1 on and off. Stop key 36 stops the collection in the event of an emergency. Alarm light 37 comes on in order to warn the user of faulty functioning, for example when the flow of fluid being collected is not situated within the authorized range, the values of which are between 30 and 350 milliliters per minute, in particular between 50 and 250 milliliters per minute. Navigation keys 38 enable the user to navigate in the various menus offered by machine 1, the principal menus relating to modification of the operating parameters, the performance of a self-test and the performance of fluid collection.

Machine 1 may also include connectors provided at area 40 for inputting and outputting data to a printer, a barcode reader or a microcomputer, as depicted in FIG. 4B.

Placement of bag system 2 in the placement device of machine 1, as depicted in FIG. 3, may be facilitated by the formation of a loop, when the system is manufactured, associating first tube 6 and second tube 8, using association device 27. This association device consists of straight connector 28 in the form of a cylindrical housing in which second tube 8 is inserted, and lateral clip 29 in the form of a U in which tube 6 is clipped, thus allowing first tube 6 and second tube 8 to be fixed together.

In order to fix tubes 6 and 8 to each other, assembly of the tubes and association device 27 may be carried out for example by solvent bonding.

The loop thus formed facilitates the positioning of the bag system on collection machine 1 and serves as a foolproof locating device because it can be positioned only in one direction in the placement device.

This loop also prevents the movement of second tube 8 by peristaltic pump 22 because association device 27 and three-way junction 7 are locked in housings provided for this purpose in groove 26 of collection machine 1 when the straight connector is integrated in second tube 8 and tubes 6 and 8 are attached to each other. When a tube is moved by rotation of the peristaltic pump, the circulation of the fluid within this tube is interfered with. The immobilization of second tube 8 therefore allows optimum functioning of peristaltic pump 22.

According to one embodiment, the part of second tube 8 situated between connector 7 and association device 27 has appropriate physical characteristics so as to correctly control the flow created by peristaltic pump 22.

For example, the part of second tube 8 forming the loop may have a hardness less than that of first tube 6. In particular, second tube 8 may have a hardness of between 60 and 70 Shore A, in particular 65 Shore A. The other tubes may have a hardness greater than 70 Shore A, in particular 78.

Figure 5:
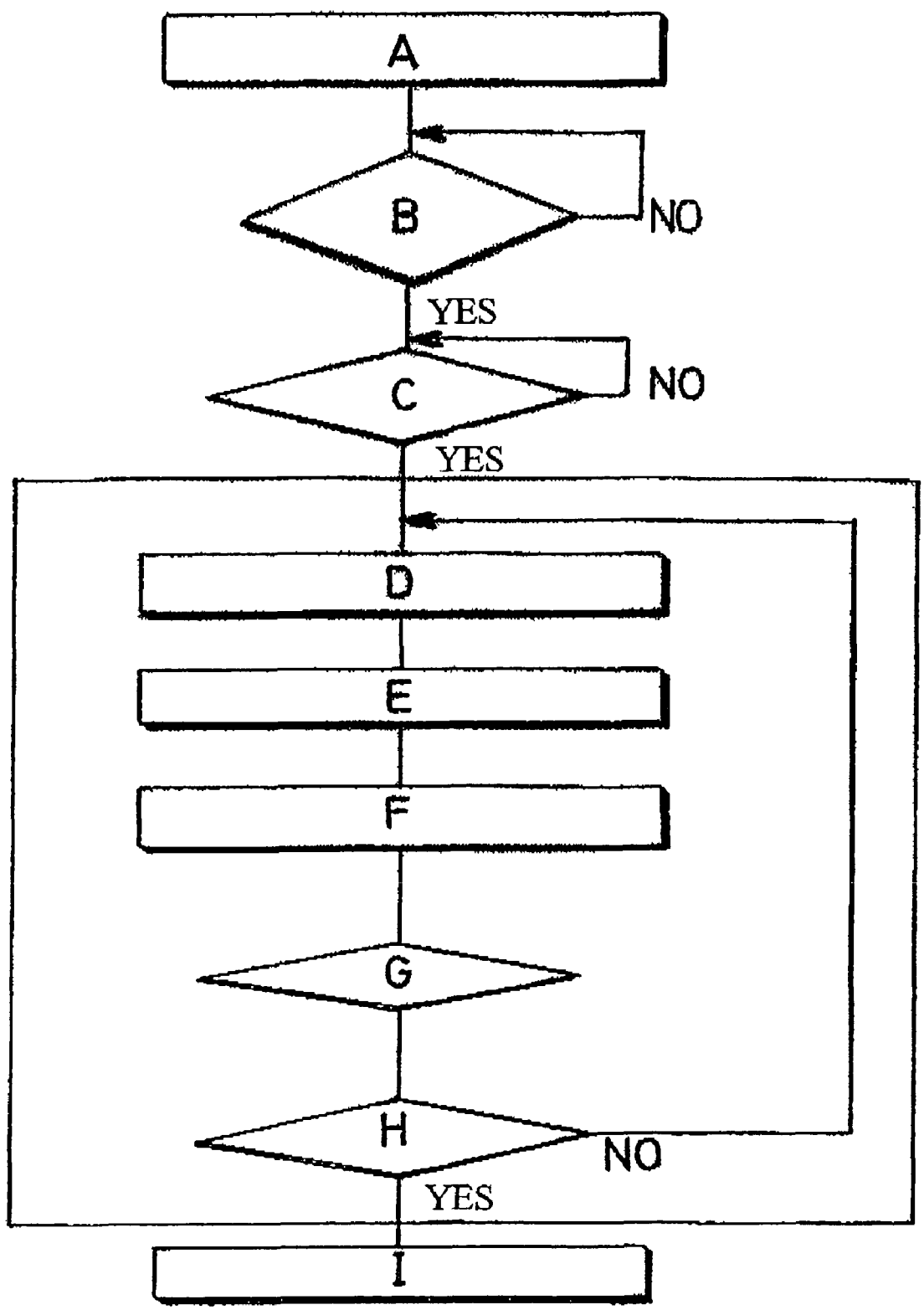
FIG. 5 depicts a flow diagram relating to the functioning of the collection machine for obtaining the given ratio between the quantity of fluid collected and the quantity of anticoagulant and/or preservation solution added.

FIG. 5 is a flow diagram relating to the function of the collection machine in obtaining the desired ratio between the quantity of fluid, such as blood, collected and the quantity of anticoagulant and/or preservation solution added.

To start collection machine 1, the user presses standby key 35. Using navigation keys 38, the user next chooses the main menu relating to collection. Display 32 indicates that it is possible to proceed with the installation of bag system 2. Then the user closes cover 34. Using information gathered by sensors 24 and 25, display 32 states whether bag system 2 is correctly placed.

Before beginning the collection process, machine 1 performs an initialization step (A).

Machine 1 causes the anticoagulant solution to circulate as far as connector 7, which makes it possible to collect blood without the risk of coagulation. Sensor 25 detects the presence of anticoagulant and/or preservation solution in order to check whether this has reached connector 7. It is possible to cause peristaltic pump 22 to make at least one additional rotation after sensor 25 has detected the presence of the solution, so that the anticoagulant and/or preservation solution is present within first tube 6 before the blood circulates therein.

During this step (A), the user introduces collection device 3 into the vein of the donor and then proceeds with the collection of biological fluid using lateral sampling device 10 associated with sampling bag 9 and clamps 13 and 14.

When this step (A) is correctly performed, display 32 indicates that the collection process may be initiated.

The step of initiating the collection process (B) commences with the opening of automatic clamp 39, when the user presses on corresponding navigation key 38.

The blood detection step (C) is performed using optical sensor 24. This optical sensor 24 detects the presence of blood in order to check that the blood is present in first tube 6 level with sensor 24. It is thus possible to estimate that the fluid is circulating suitably within first tube 6.

In step (D), machine 1 uses weighing device 21, peristaltic pump 22 and control electronics 23 in order to obtain a desired ratio between the quantity of blood collected and the quantity of anticoagulant and/or preservation solution added.

The step of calculating the variation in weight of fluid collected (D) is performed by weighing device 21. Step (E), calculating the flow rate of blood, is performed using the results obtained during step (D). Steps (F) and (G) concern respectively the adjustment of the speed of rotation of peristaltic pump 22 and the verification of the flow rate of blood. Concerning the adjustment of the speed of peristaltic pump 22, control electronics 23 calculate, from the flow rate obtained at step (E), the flow rate for anticoagulant solution to be obtained. In particular, the ratio between the quantity of anticoagulant and/or preservation solution and that of biological fluid may be fixed at 1/7. Control electronics 23 next transcribe the desired solution flow rate into a certain speed of rotation of peristaltic pump 22. The frequency of adjustment of the speed of rotation of peristaltic pump 22 is such that the period between two adjustments is less than one second, more particularly around a tenth of a second.

Step (H) concerns obtaining of the programmed volume of blood and is performed by weighing device 21. The programmed volume corresponds to a certain weight, and when weighing device 21 measures this weight, the collection process stops. As long as this weight is not attained, machine 1 continues the loop consisting of steps (D) to (G).

Step (I) marks the end of the collection process.

The volume of blood collected is variable according to the geographic area. One advantage of the device according to the invention is that it is possible to choose the volume of blood collected at the time of collection, and that it is not necessary to provide different bag systems containing different volumes of anticoagulant. Moreover, should the user have to interrupt the collection process before the programmed end of the collection process, by pressing on stop key 36, the blood is usable because the ratio between the quantity of blood collected and the quantity of anticoagulant and/or preservation solution is correct throughout the collection process.

The invention claimed is:

1. A method of collecting a biological fluid comprising:
   collecting a biological fluid by natural flow from a patient, without a pump;
   measuring a natural fluid flow rate of the biological fluid; and
   pumping anticoagulant and/or preservation solution from a reservoir to the collected biological fluid at a solution flow rate;
   wherein:
   measuring the natural fluid flow rate of the biological fluid comprises weighing the collected biological fluid from the patient, the pumped anticoagulant and/or preservation solution, and any anticoagulant and/or preservation solution remaining in the reservoir; and
   the solution flow rate is adjusted while collecting the biological fluid from the patient based upon the measured natural fluid flow rate to preserve a selected ratio between the collected biological fluid and the anticoagulant and/or preservation solution.

2. The method of claim 1, further comprising:
   collecting the biological fluid in a collection bag; and
   pumping the anticoagulant and/or preservation solution to the collection bag;
   wherein the solution flow rate is adjusted while collecting the biological fluid from the patient based upon the measured fluid flow rate to preserve a selected ratio in the collection bag between the collected biological fluid and the anticoagulant and/or preservation solution.

3. The method of claim 1, wherein the biological fluid comprises blood.

4. The method of claim 1, wherein measuring a fluid flow rate of the biological fluid further comprises calculating a variation in weight of the collected biological fluid, the pumped anticoagulant and/or preservation solution, and any anticoagulant and/or preservation solution remaining in the reservoir.

5. The method of claim 1, wherein pumping comprises:
   pumping using a peristaltic pump having a variable rotation speed; and
   adjusting the variable rotation speed to obtain the appropriate solution flow rate.

6. The method of claim 2, further comprising:
   collecting the biological fluid with a collection device in fluid communication with the collection bag via a tube; and
   detecting the presence of the biological fluid in the tube.

7. The method of claim 6, wherein detecting the presence of the biological fluid in the tube comprises optical or ultrasonic sensing.

8. The method of claim 2, further comprising collecting a second sample of the biological fluid by natural flow, without a pump.

9. A method of collecting a blood, comprising:
   collecting blood by natural flow from a patient, without a pump;
   measuring a natural fluid flow rate of the blood collected from the patient, the natural flow being based on venous pressure and gravity; and
   pumping anticoagulant and/or preservation solution from a reservoir to the collected blood at a solution flow rate;
   wherein:
   measuring the natural fluid flow rate of the blood comprises weighing the collected blood from the patient, the pumped anticoagulant and/or preservation solution, and any anticoagulant and/or preservation solution remaining in the reservoir; and
   the solution flow rate is adjusted while collecting the blood based upon the measured fluid flow rate to preserve a selected ratio between the collected blood and the anticoagulant and/or preservation solution.

10. The method of claim 9, further comprising:
    collecting the blood in a collection bag; and
    pumping the anticoagulant and/or preservation solution to the collection bag;
    wherein the solution flow rate is adjusted while collecting the blood from the patient based upon the measured fluid flow rate to preserve a selected ratio in the collection bag between the collected blood and the anticoagulant and/or preservation solution.

11. The method of claim 9, wherein measuring a fluid flow rate of the blood further comprises calculating a variation in weight of the collected blood, the pumped anticoagulant and/or preservation solution, and any anticoagulant and/or preservation solution remaining in the reservoir.

12. The method of claim 9, wherein pumping comprises:
    pumping using a peristaltic pump having a variable rotation speed; and
    adjusting the variable rotation speed to obtain the appropriate solution flow rate.

* * * * *